United States Patent [19]

Asselin et al.

[11] 4,304,772

[45] Dec. 8, 1981

[54] ETHANOCARBAZOLE DERIVATIVES AND ANTIDEPRESSANT COMPOSITIONS

[75] Inventors: Andre A. Asselin, St. Laurent; Leslie G. Humber, Dollard des Ormeaux, both of Canada

[73] Assignee: Ayerst, McKenna & Harrison, Inc., Montreal, Canada

[21] Appl. No.: 218,329

[22] Filed: Dec. 19, 1980

[51] Int. Cl.$^3$ .................... A61K 31/54; A61K 31/40; C07D 209/86; C07D 209/88
[52] U.S. Cl. ................... 424/246; 424/248.4; 424/250; 424/267; 424/274; 544/60; 544/142; 544/372; 546/200; 260/315
[58] Field of Search .................. 260/315; 546/200; 544/60, 142, 372; 424/246, 248.4, 250, 267, 274

[56] References Cited

PUBLICATIONS

Derwent Publications Ltd., Farmdoc 49955C, DT 28549 41, 10-7-80 (Germany).
R. Robinson and J. E. Saxton, J. Chem. Soc., 2596 (1953).
H. Plieninger et al., Chem. Abstr., 60 11997c (1964) for Chem. Ber., 97,667 (1964).

Primary Examiner—Henry R. Jiles
Assistant Examiner—R. W. Ramsuer
Attorney, Agent, or Firm—Arthur E. Wilfond

[57] ABSTRACT

Herein is disclosed ethanocarbazole derivatives, acid addition salts thereof, processes for their preparation, methods of using the derivatives and pharmaceutical compositions of the derivatives. The derivatives are useful for treating depression in a mammal and are represented by the following formula

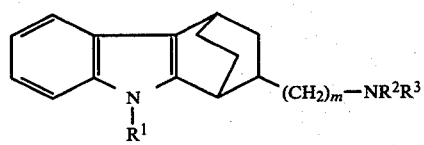

in which $R^1$ is hydrogen or lower alkyl, $R^2$ and $R^3$ each is hydrogen or lower alkyl or $R^2$ and $R^3$ together with the nitrogen atom form a 1-pyrrolidinyl, 1-piperidinyl, 1-piperazinyl, 4-morpholinyl or 4-thiomorpholinyl ring, and m is an integer from 0 to 3.

13 Claims, No Drawings

ETHANOCARBAZOLE DERIVATIVES AND ANTIDEPRESSANT COMPOSITIONS

BACKGROUND OF THE INVENTION

This invention relates to novel ethanocarbazole derivatives, to therapeutically acceptable acid addition salts thereof, to processes for their preparation, to methods of using the derivatives and to pharmaceutical compositions of the derivatives. The derivatives are useful for treating depression in a mammal.

The applicants are aware of ethanocarbazole derivatives, as exemplified by R. Robinson and J. E. Saxton, J. Chem. Soc., 2596 (1953), H. Plieninger et al., Chem. Abstr. 60 11997c (1964) for Chem. Ber., 97, 667 (1964) and Derwent Publications Ltd., Farmdoc 49955 C for German Pat. No. 2,854,941 July 10, 1980, which are believed to be the most closely related compounds to the compounds of this invention. However, these reported compounds lack the substitutents on the ethanocarbazole ring, which are characteristic of the compounds of this invention.

SUMMARY OF THE INVENTION

The compounds of this invention are represented by formula I

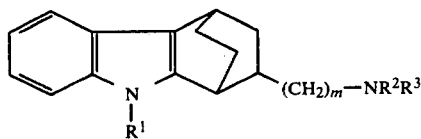

(I)

in which $R^1$ is hydrogen or lower alkyl, $R^2$ and $R^3$ each is hydrogen or lower alkyl or $R^2$ and $R^3$ together with the nitrogen atom form a 1-pyrrolidinyl, 1-piperidinyl, 1-piperazinyl, 4-morpholinyl or 4-thiomorpholinyl ring, and m is an integer from 0 to 3; or a therapeutically acceptable acid addition salt thereof.

A preferred group of compounds of this invention is represented by formula I in which $R^1$, $R^2$ and $R^3$ each is hydrogen or lower alkyl, and m is the integer 0 or 1; or a therapeutically acceptable acid addition salt thereof.

A most preferred group of compounds of this invention is represented by formula I in which $R^1$ is hydrogen or lower alkyl, $R^2$ and $R^3$ each is lower alkyl, and m is the integer 1; or a therapeutically acceptable acid addition salt thereof.

A pharmaceutical composition is provided by combining the compound of formula I, or a therapeutically acceptable acid addition salt thereof, and a pharmaceutically acceptable carrier.

The compounds of this invention can be used to treat depression in a depressed mammal by administering to the mammal an effective antidepressive amount of a compound of formula I or a therapeutically acceptable acid addition salt thereof.

DETAILED DESCRIPTION OF THE INVENTION

The term "lower alkyl" as used herein means straight chain alkyl radicals containing from one to six carbon atoms and branched chain alkyl radicals containing three or four carbon atoms and includes methyl, ethyl, propyl, 1-methylethyl, butyl, 1,1-dimethylethyl, pentyl and hexyl.

The term "lower alkanol" as used herein means both straight and branched chain alkanols containing from one to four carbon atoms and includes methanol, ethanol, 1-methylethanol and butanol.

The term "organic proton acceptor" as used herein means the organic bases or amines, for instance, triethylamine, pyridine, N-ethylmorpholine and 1,5diazabicyclo[4.3.0]non-5-ene.

The term "inorganic proton acceptor" as used herein means the inorganic bases, preferably the alkali methyl hydroxides, carbonates and bicarbonates, for example, sodium hydroxide, potassium hydroxide, sodium carbonate, sodium bicarbonate and potassium carbonate.

The term "proton acceptor" as used herein means a proton acceptor selected from an organic proton acceptor and inorganic proton acceptor, as defined hereinabove.

The term "complex metal hydride" as used herein means metal hydride reducing agents and includes, for example, lithium aliuminum hydride, lithium aluminum hydride-aluminum chloride, aluminum hydride-aluminum chloride, diborane, diisobutylaluminum hydride, borane methyl sulfide and sodium borohydride-aluminum chloride.

The term "complex borohydride" as used herein means the metal borohydrides and includes, for example, sodium borohydride, potassium borohydride, lithium borohydride and zinc borohydride.

The compounds of this invention are capable of forming acid addition salts with therapeutically acceptable acids. The acid addition salts are prepared by reacting the base form of the appropriate compound of formula I with one or more equivalents, preferably with an excess, of the appropriate acid in an organic solvent, for example, diethyl ether or an ethanol-diethyl ether mixture.

These salts, when administered to a mammal, possess the same pharmacologic activities as the corresponding bases. For many purposes it is preferable to administer the salts rather than the base compounds. Suitable acids to form these salts include the common mineral acids, e.g. hydrohalic, sulfuric or phosphoric acid; the organic acids, e.g. maleic, citric or tartaric acid; and acids which are sparingly soluble in body fluids and which impart slow-release properties to their respective salts, e.g. pamoic or tannic acid or carboxymethyl cellulose. The addition salts thus obtained are the functional equivalent of the parent base compound in respect to their therapeutic use. Hence, these addition salts are included within the scope of this invention and are limited only by the requirement that the acids employed in forming the salts be therapeutically acceptable.

Also included in this invention are the stereochemical isomers of the compounds of formula I which result from asymmetric centers contained therein. These isomeric forms may be prepared by chemical methods and are purified readily by crystallization or chromatography.

Individual optical isomers, which might be separated by fractional crystallization of the diastereoisomeric salts formed thereof, for instance, with d- or l-tartaric acid or D-(+)-α-bromocamphor sulfonic acid, are also included.

The compounds of formula I are central nervous system agents exhibiting antidepressant activity of the type exhibited by amitriptyline, nortriptyline and imipramine. The antidepressant activity of the compounds of formula I, or their acid addition salts with therapeutically acceptable acids, is demonstrated in standard pharmacologic tests such as, for example, the test described by P. V. Petersen et al., Acta. Pharmacol. Toxicol., 24, 121 (1966).

More specifically, as noted in the above reference, the antidepressant properties of a compound can be demonstrated by its capacity to prevent the depressant effects of reserpine. Furthermore, it is well documented that reserpine in animals produces a model depression which can be used for detecting antidepressant properties. Accordingly, the compounds of formula I are shown to be effective antidepressant agents by a modification of the prevention of the reserpine-induced ptosis in mice, described by P. V. Petersen et al., cited above.

In this method, male albino mice weighing from 18–24 grams are used. A solution of 0.4 mg/ml of reserpine is prepared. This is administered subcutaneously to a group of ten mice at a volume of 0.2 ml/20 g (4 mg/kg) of body weight. Immediately following this, the same animals are injected intraperitoneally with the test compound solution.

A control is established by substituting saline solution for the test compound in the above procedure.

After 90 minutes, the mice are successively lifted from their cages by their tails, shaken and placed on the table. Their eyes are then inspected for ptosis. The number of animals with open eyes is noted. The observation is based on all or none response. The animals with open eyes are considered to be protected from reserpine-induced ptosis.

Using the above method, the compounds of the present invention prevent ptosis in mice at doses ranging from about 0.5 to 200 mg per kilogram of body weight. For example, the following compound of formula I is an effective antidepressant agent when administered intraperitoneally to the mouse (the effective i.p. dose to prevent ptosis in 50% of the animals in mg per kilogram of body weight is given in the parentheses): 2-[(dimethylamino)methyl]-1,2,3,4-tetrahydro-9-methyl-1,4-ethanocarbazole hydrochloride (described in Example 5, at a dose of 0.8–1.4 mg/kg).

In a modification of the above test, reserpine at a dose of 3 mg per kilogram of body weight is injected subcutaneously 60 minutes after the test compound. Ninety minutes after the injection of reserpine, the mice are inspected for ptosis. Using this method, the following compounds of formula I are effective antidepressant agents when administered intraperitoneally to the mouse (the effective i.p. dose to prevent ptosis in 50% of the animals in mg per kg of body weight is given in the parentheses): 2-[(dimethylamino)methyl]-9-ethyl-1,2,3,4-tetrahydro-1,4-ethanocarbazole hydrochloride (described in Example 5, at a dose of 1.3–2.6 mg/kg) and 9-ethyl-1,2,3,4-tetrahydro-N,N-dimethyl-1,4-ethanocarbazole-2-amine (described in Example 8, at a dose of 30 mg/kg).

When the compounds of formula I of this invention are used as antidepressant agents in mammals, e.g. rats and dogs, they are used alone or in combination with pharmacologically acceptable carriers, the proportion of which is determined by the solubility and chemical nature of the compound, chosen route of administration and standard biological practice. For example, they are administered orally in solid form, e.g., capsule or tablet. They can also be administered orally in the form of suspensions or solutions or they can be injected parenterally. For parental administration they are used in the form of a sterile solution containing other solutes, for example, enough saline or glucose to make the solution isotonic.

The tablet compositions contain the active ingredient in admixture with non-toxic pharmaceutical excipients known to be suitable in the manufacture of tablets. Suitable pharmaceutical excipients are, for example, starch, milk sugar or certain types of clay. The tablets can be uncoated or they can be coated by known techniques so as to delay disintegration and absorption in the gastrointestinal tract and thereby provide a sustained action over a longer period.

The aqueous suspensions of the invention contain the active ingredient in admixture with one or more non-toxic pharmaceutical excipients known to be suitable in the manufacture of aqueous suspensions.

Suitable excipients are, for example, methyl-cellulose, sodium alginate, gum acacia or lecithin. The aqueous suspensions can also contain one or more flavoring agents and one or more sweetening agents.

Non-aqueous suspensions can be formulated by suspending the active ingredient in a vegetable oil, for example, arachis oil, olive oil, sesame oil, or coconut oil, or in a mineral oil. The suspension can contain a thickening agent, for example beeswax, hard paraffin or cetyl alcohol. These compositions can also contain a sweetening agent, flavoring agent and antioxidant.

The dosage of the compounds of formula I of this invention as antidepressant agents will vary with the form of administration and the particular compound chosen. Furthermore, it will vary with the particular host, as well as the age and condition of the host under treatment. Generally, treatment is initiated with small dosages substantially less than the optimum dose of the compound. Thereafter, the dosage is increased by small increments until the optimum effect under the circumstances is reached. In general, the compounds of this invention are most desirably administered at a concentration level that will generally afford effective results without causing any harmful or deleterious side effects. The effective antidepressant amount of the compounds usually ranges from about 0.1 mg to about 300 mg per kilogram of body weight per day, although as aforementioned variations will occur. However, a dosage level that is in the range of from about 0.5 mg to about 100 mg per kilogram of body weight per day is employed most desirably in order to achieve effective results.

The compounds of formula I are prepared in the following manner.

Reaction scheme I illustrates a method for preparing a 1,2,3,4-tetrahydro-1,4-ethanocarbazole-2-carboxylic acid of formula IV, which is used as an intermediate in the synthesis of the compounds of formula I

REACTION SCHEME 1

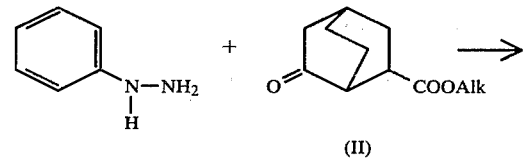

(II)

-continued

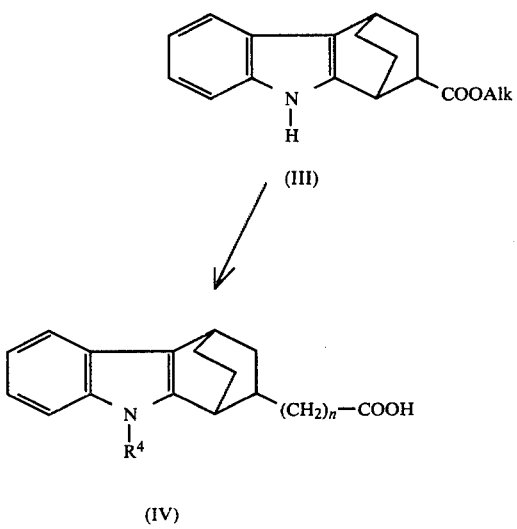

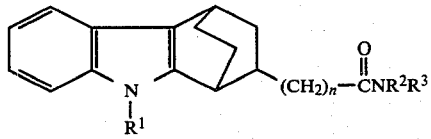

The 1,2,3,4-tetrahydro-1,4-ethanocarbazole ring system is prepared by the Fisher indole synthesis wherein phenylhydrazine is condensed with a bicyclooctane of formula II in which Alk is lower alkyl to obtain the corresponding compound of formula III in which Alk is as defined herein. The indole synthesis is achieved by maintaining a solution of about equal molar quantities of phenylhydrazine and the bicyclooctane of formula II in acetic acid at about 100° to 120° C. for about five hours. The bicyclooctanes of formula II can be prepared by following the procedure described by D. Varech and J. Jacques, Tetrahedron, 28, 5671 (1972).

Alkaline hydrolysis of the compound of formula III, preferably with about an equimolar amount of potassium carbonate in a solution of a lower alkanol and water at 80° to 100° C. for about four hours, gives the corresponding acid of formula IV in which $R^4$ is hydrogen and n is the integer 0.

Alkylation of the compound of formula IV in which $R^4$ is hydrogen and n is the integer 0 gives the corresponding compound of formula IV in which $R^4$ is lower alkyl and n is the integer 0. A convenient method of alkylation is the reaction of the compound of formula IV in which $R^4$ is hydrogen and n is the integer 0 with about two molar equivalents of sodium hydride in an inert solvent, preferably tetrahydrofuran, at 20° to 30° C. for 10 to 30 minutes to generate the corresponding anion. Reaction of this anion with a lower alkyl iodide, chloride or bromide at 20° to 60° C. for 5 to 30 hours gives the corresponding compound of formula IV in which $R^4$ is lower alkyl and n is the integer 0.

Similarly, reaction of the compound of formula IV in which $R^4$ is hydrogen and n is the integer 0 with sodium hydride and benzyl bromide gives the corresponding compound of formula IV in which $R^4$ is benzyl and n is the integer 0.

In turn, the acid of formula IV in which $R^4$ is hydrogen or lower alkyl and n is the integer 0 is converted to the corresponding amide of formula V in which $R^1$, $R^2$ and $R^3$ are as defined herein and n is the integer 0.

The first step in this conversion involves the formation of the corresponding mixed anhydride from the acid. The mixed anhydride is formed by reacting the acid of formula IV in which $R^4$ is hydrogen or lower alkyl and n is the integer 0 with about three molar equivalents of ethyl chloroformate in the presence of about one molar equivalent of an organic proton acceptor in an inert organic solvent, preferably chloroform or tetrahydrofuran, at 0° to 30° C. for two to five hours. An excess of an amine of formula $HNR^2R^3$ wherein $R^2$ and $R^3$ are as defined herein is added to the solution containing the mixed anhydride. The resulting solution is allowed to stand at 20° to 30° C. for 20 to 30 hours and the corresponding amide of formula V is isolated.

Reduction of the amide of formula V in which $R^1$, $R^2$ and $R^3$ are as defined herein and n is the integer 0 with a complex metal hydride gives the corresponding compound of formula I in which $R^1$, $R^2$ and $R^3$ are as defined herein and m is the integer 1. A preferred complex metal hydride is lithium aluminum hydride. For reduction, a suspension of the amide of formula V and about an equivalent molar amount of lithium aluminum hydride in an inert anhydrous organic solvent, preferably tetrahydrofuran, diethyl ether or xylene, is stirred at 20° to 140° C. for one to five hours and the compound of formula I is isolated.

Reaction of the acid of formula IV in which $R^4$ is as defined herein and n is the integer 0 with ethyl chloroformate, in the same manner as described above, gives a solution containing the corresponding mixed anhydride. An excess of sodium azide is added to the solution at about $-10°$ C. and the resulting solution is maintained at about $-10°$ C. for about one hour and the corresponding carbonyl azide is isolated. A solution of the carbonyl azide in an inert organic solvent, preferably benzene, is maintained at 80° to 100° C. for two to five hours and the corresponding isocyanic acid is recovered.

Reduction of the isocyanic acid with a complex borohydride gives the corresponding compound of formula VI in which $R^4$ is as defined herein and $R^2$ is hydrogen. In a preferred mode of reduction, a suspension of the

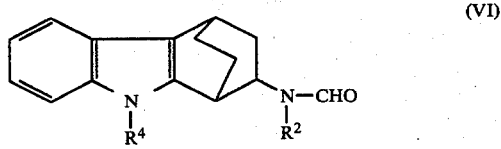

isocyanic acid and about three molar equivalents of sodium borohydride in an inert organic solvent, preferably dimethoxyethane, is stirred at 20° to 30° C. for 20 to 30 hours and the compound of formula VI is isolated.

Alkylation of the compound of formula VI in which $R^4$ is lower alkyl or benzyl and $R^2$ is hydrogen, in the same manner as described above, gives the corresponding compound of formula VI in which $R^4$ is lower alkyl or benzyl and $R^2$ is lower alkyl.

Catalytic hydrogenation of the compound of formula VI in which $R^4$ is benzyl and $R^2$ is lower alkyl under an atmosphere of hydrogen in the presence of a hydrogenation catalyst gives the corresponding compound of formula VI in which $R^4$ is hydrogen and $R^2$ is lower alkyl. Catalysts include the noble metal catalyst, e.g. platinum, platinum oxide, palladium or palladium oxide. The hydrogenation can be accomplished conveniently using five to ten percent palladium on charcoal, in an inert organic solvent, preferably methanol or ethanol, to obtain the corresponding compound of formula VI in which $R^4$ is hydrogen and $R^2$ is lower alkyl.

Reduction of the compound of formula VI in which $R^2$ and $R^4$ each is hydrogen or lower alkyl with a complex metal hydride, preferably with lithium aluminum hydride in the same manner as described above, gives the corresponding compound of formula I in which $R^1$ and $R^2$ each is hydrogen or lower alkyl, $R^3$ is methyl and m is the integer 0.

Alkaline hydrolysis of the compound of formula VI in which $R^2$ and $R^4$ each is hydrogen or lower alkyl gives the corresponding compound of formula I in which $R^1$ and $R^2$ each is hydrogen or lower alkyl, $R^3$ is hydrogen and m is the integer 0. For the hydrolysis, a solution of the compound of formula VI and an excess of sodium or potassium hydroxide in a mixture of water and a lower alkanol, preferably ethanol, is maintained at 75° to 100° C. for three to ten hours and the compound of formula I is isolated.

Similarly, alkaline hydrolysis of the compound of formula VI in which $R^4$ is benzyl and $R^2$ is hydrogen or lower alkyl gives the corresponding compound of formula VII in which $R^2$ is hydrogen or lower alkyl, $R^3$ is hydrogen and $R^4$ is benzyl.

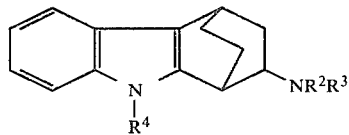

(VII)

Alkylation of the compound of formula VII in which $R^2$ is lower alkyl, $R^3$ is hydrogen and $R^4$ is benzyl with a lower alkyl iodide, chloride or bromide, in the same manner as described above, gives the corresponding compound of formula VII in which $R^2$ and $R^3$ each is lower alkyl and $R^4$ is benzyl. Catalytic hydrogenation of the latter compound, in the same manner as described above, gives the corresponding compound of formula I in which $R^1$ is hydrogen, $R^2$ and $R^3$ each is lower alkyl and m is the integer 0.

Alkylation of the compound of formula I in which $R^1$ and $R^2$ are lower alkyl, $R^3$ is hydrogen and m is the integer 0 with a lower alkyl iodide, chloride or bromide, in the same manner as described above, gives the corresponding compound of formula I in which $R^1$, $R^2$ and $R^3$ each is lower alkyl and m is the integer 0.

Reductive amination of the compound of formula I in which $R^1$ is lower alkyl, $R^2$ and $R^3$ are hydrogen and m is the integer 0 with a dialdehyde of formula $HCO(CH_2)_2CHO$, $HCO(CH_2)_3CHO$, $HCOCH_2NHCH_2CHO$, $HCOCH_2O\text{-}CH_2CHO$ or $HCOCH_2SCH_2CHO$ in the presence of sodium cyanoborohydride in the manner described by R. F. Borch et al., J. Amer. Chem. Soc., 93, 2897 (1971) gives the corresponding compound of formula I in which $R^1$ is lower alkyl, $R^2$ and $R^3$ together with the nitrogen atom form a 1-pyrrolidinyl, 1-piperidinyl, 1-piperazinyl, 4-morpholinyl or 4-thiomorpholinyl ring and m is the integer 0.

Similarly, reductive amination of the compound of formula VII in which $R^4$ is benzyl and $R^2$ and $R^3$ are hydrogen with the same dialdehydes, followed by catalytic hydrogenation, gives the corresponding compound of formula I in which $R^1$ is hydrogen, $R^2$ and $R^3$ together with the nitrogen atom form a 1-pyrrolidinyl, 1-piperidinyl, 1-piperazinyl, 4-morpholinyl or 4-thiomorpholinyl ring and m is the integer 0.

Chain extension of the carboxylic acid of formula IV in which $R^4$ is benzyl or lower alkyl and n is 0 provides corresponding carboxylic acids of formula IV in which $R^4$ is benzyl or lower alkyl and n is 1 or 2. The first step in this chain extension involves reduction of the carboxylic acid of formula IV in which $R^4$ is benzyl or lower alkyl and n is 0 with lithium aluminum hydride, in the same manner as described above, to obtain the corresponding methanol derivative. Reaction of this methanol derivative with phosphorus tribromide gives the corresponding methyl bromide derivative. This derivative is reacted with magnesium and carbon dioxide, according to the Grignard method, to obtain the corresponding carboxylic acid of formula IV in which $R^4$ is benzyl or lower alkyl and n is 1. For the preparation of another carboxylic acid of formula IV, the above noted methyl bromide derivative is condensed with the anion of malonic acid to obtain the corresponding dicarboxylic acid derivative. Removal of one of the carboxylic acids by decarboxylation, preferably with aqueous sulfuric acid at 50° to 100° C., gives the corresponding carboxylic acid of formula IV in which $R^4$ is benzyl or lower alkyl and n is 2. Catalytic hydrogenation of the carboxylic acid of formula IV in which $R^4$ is benzyl and n is 1 or 2, in the same manner as described above, gives the corresponding compound of formula IV in which $R^4$ is hydrogen and n is 1 or 2.

Amidation of the compound of formula IV in which $R^4$ is hydrogen or lower alkyl and n is 1 or 2, in the same manner as described above, gives the corresponding amide of formula V in which $R^1$, $R^2$ and $R^3$ are as defined herein and n is 1 or 2.

Reduction of the latter compound of formula V with a complex metal hydride, in the same manner as described above, gives the corresponding compound of formula I in which $R^1$, $R^2$ and $R^3$ are as defined herein and m is 2 or 3.

The following examples illustrate further this invention.

EXAMPLE 1

1,2,3,4-Tetrahydro-1,4-ethanocarbazole-2-carboxylic Acid Methyl Ester (III: Alk=methyl)

A solution of 2-oxo-6-endo-bicyclo[2.2.2]octanecarboxylic acid methyl ester [15.0 g, 0.082 mole, described by D. Varech and J. Jacques, Tetrahedron, 28, 5671 (1972)] and phenylhydrazine hydrochloride (15.0 g, 0.10 mole) in acetic acid (300 ml) was refluxed for 5 hr. The hot reaction mixture was poured on crushed ice and water and extracted with diethyl ether. The organic layer was washed very carefully with sodium bicarbonate and saturated sodium chloride solution. After drying over magnesium sulfate, it was evaporated to dryness affording a yellow foam (17.5 g). The foam was chromatographed through a silica gel column (550 g) using a 3% acetone-benzene mixture as eluant. The title ester (13.0 g) was obtained as a yellow foam which was used as such for the next step. The foam crystallized upon standing overnight and a small amount was recrystallized from hexane-diethyl ether: mp 129°–130° C. and NMR (CDCl$_3$) δ 1.1–1.9 (m, 6H), 2.15 (m, 1H), 2.90 (m, 1H), 3.55 (m, 1H), 3.45 (s, 3H), 6.9–7.6 (m, 4H) and 8.2 (br, 1H).

EXAMPLE 2

1,2,3,4-Tetrahydro-1,4-ethanocarbazole-2-carboxylic Acid (IV: $R^4$=H and n=0)

A mixture of 1,2,3,4-tetrahydro-1,4-ethanocarbazole-2-carboxylic acid methyl ester (13.0 g, 0.05 mole, described in Example 1), potassium carbonate (7.0 g, 0.05 mole), methanol (160 ml) and water (40 ml) was refluxed for 4 hr (oil bath at 90° C.) and stirred at room temperature for 18 hr. The reaction mixture was poured into water (500 ml) and washed with diethyl ether (2×). The aqueous phase was acidified with hydrochloric acid 1N (100 ml) and extracted with diethyl ether (3×). Organic layers were washed with a saturated sodium chloride solution, dried and evaporated to dryness to afford the title compound (12 g). Crystallization afforded a total of 7.5 g of title compound: mp 212°–214° C.; NMR (DMSO-d$_6$) δ 1.7 (m, 6H), 2.8 (m, 1H), 3.5 (m, 2H), 6.7–7.5 (m, 4H), 10.9 (s, 1H) and 11.8 (br, 1H); and Anal. Calcd for C$_{15}$H$_{15}$O$_2$N: C, 74.66% H, 6.27% N, 5.81% and Found: C, 74.67% H, 6.48% N, 5.80%.

EXAMPLE 3

1,2,3,4-Tetrahydro-9-methyl-1,4-ethanocarbazole-2-carboxylic Acid (IV: $R^4$=methyl and n=0)

A solution of 1,2,3,4-tetrahydro-1,4-ethanocarbazole-2-carboxylic acid (6.5 g, 0.027 mole, described in Example 2) in dry tetrahydrofuran (100 ml) was added dropwise under nitrogen to a stirred suspension of sodium hydride (3.0 g, 0.06 mole, 50% dispersion) in dry tetrahydrofuran (100 ml). The temperature was kept below 25° C. during the addition and the reaction mixture was stirred at this temperature for 15 min after the end of the addition. Methyl iodide (5 ml) was then added with a dropping funnel. The reaction was initiated by heating the reaction mixture at 40° C. on a steam bath which was removed as soon as this temperature was reached. After stirring at room temperature for 18 hr, water was added very cautiously to destroy excess sodium hydride and then more water (400 ml) was added. This solution was washed with diethyl ether (300 ml). The aqueous layer was acidified with 1.4 N hydrochloric acid (65 ml) and extracted three times with diethyl ether. These organic layers were dried over magnesium sulfate and filtered in the presence of charcoal through diatomaceous earth. Evaporation of the solvents afforded a yellow oil (6.0 g) which was chromatographed through a silica gel column (300 g) using 10% acetone-benzene as eluant affording the title compound (4.5 g) which was crystallized out of a benzene-hexane mixture: mp 179°–182° C.; NMR (CDCl$_3$) δ 3.66 (s, 3H) and 7.0–7.6 (m, 4H); and Anal. Calcd for C$_{16}$H$_{17}$N$_2$: C, 75.27% H, 6.71% N, 5.49% and Found: C, 75.51% H, 6.71% N, 5.75%.

In the same manner, but replacing methyl iodide with an equivalent amount of ethyl iodide or propyl iodide, the following acids of formula IV were obtained, respectively: 9-ethyl-1,2,3,4-tetrahydro-1,4-ethanocarbazole-2-carboxylic acid: mp 142°–143° C. (crystallized from benzene-diethyl ether); NMR (CDCl$_3$) δ 1.23 (t, 3H), 1.7 (m, 6H), 2.8 (m, 1H), 3.55 (m, 2H), 4.12 (q, 2H), 7.3 (m, 4H) and 11.2 (br, 1H); and Anal. Calcd for C$_{17}$H$_{19}$NO$_2$: C, 75.81% H, 7.11% N, 5.20% and Found: C, 75.86% H, 7.23% N, 5.11%; and 1,2,3,4-tetrahydro-9-propyl-1,4-ethanocarbazole-2-carboxylic acid; mp 128°–130° C. (crystallized from hexanediethyl ether); NMR (CDCl$_3$) δ 0.8 (t, 3H), 1.1–2.3 (m, 8H), 2.85 (m, 1H), 3.6 (m, 2H), 4.05 (t, 2H), 7.0–7.65 (m, 4H) and 11.3 (br, 1H); and Anal. Calcd for C$_{18}$H$_{12}$NO$_2$: C, 76.29% H, 7.47% N, 4.94% and Found: C, 76.36% H, 7.59% N, 4.84%.

EXAMPLE 4

N,N-Dimethyl-1,2,3,4-tetrahydro-1,4-ethanocarbazole-2-carboxamide (V: $R^1$=H, $R^2$ and $R^3$=methyl and n=0)

To a solution of 1,2,3,4-tetrahydro-1,4-ethanocarbazole-2-carboxylic acid (1.0 g, 0.00415 mole, described in Example 2) in 10 ml chloroform stirred at 0° C., was added triethylamine (6.8 ml, 0.047 mole) followed after 10 min by dropwise addition under nitrogen of ethyl chloroformate (1.1 ml, 0.012 mole) at the same temperature. The reaction mixture was stirred at room temperature for 2.5 hr and cooled in ice. Dimethylamine gas was bubbled into the suspension for about 5 min and left stirring overnight at room temperature. The mixture was diluted with chloroform and extracted with 5% sodium carbonate, 10% hydrochloric acid, water, then dried and evaporated to dryness to yield a solid compound (850 mg) which was crystallized from methylene chloride-hexane to afford the title compound (350 mg) as colorless crystals: mp 231°–232° C.; NMR (CDCl$_3$) δ 1.1–2.5 (m, 6H), 2.7 (s, 3H), 2.85 (s, 3H), 3.1 (m, 1H), 3.5 (m, 2H), 6.9–7.6 (m, 4H), 9.2 (br, 1H); and Anal. Calcd for C$_{17}$H$_{20}$N$_2$O: C, 76.09% H, 7.51% N, 10.44% and Found: C, 75.16% H, 7.64% N, 10.24%.

In the same manner, but replacing 1,2,3,4-tetrahydro-1,4-ethanocarbazole-2-carboxylic acid with another acid of formula IV described in Example 3, the following amides of formula V were obtained: 1,2,3,4-tetrahydro-N,N,9-trimethyl-1,4-ethanocarbazole-2-carboxamide: mp 159°–162° C. (crystallized from benzene-hexane); NMR (CDCl$_3$) δ 1.1–2.0 (m, 6H), 2.3 (m, 1H), 2.8 (s, 3H), 2.95 (s, 3H), 3.5 (m, 2H), 3.85 (s, 3H) and 6.9–7.6 (m, 4H); and Anal. Calcd for C$_{18}$H$_{22}$N$_2$O: C, 76.56% H, 7.85% N, 9.92% and Found: C, 76.73% H, 7.89% N, 9.91%; 9-ethyl-1,2,3,4-tetrahydro-N,N-dimethyl-1,4-ethanocarbazole-2-carboxamide: mp 164°–166° C. (crystallized from chloroform-hexane); and 1,2,3,4-tetrahydro-N,N-dimethyl-9-propyl-1,4-ethanocarbazole-2-carboxamide; mp 118°–120° C. (crystallized from hexane-diethyl ether).

EXAMPLE 5

2-[(Dimethylamino)methyl]-1,2,3,4-tetrahydro-9-methyl-1,4-ethanocarbazole (I: $R^1$, $R^2$ and $R^3$=methyl and m=1)

A solution of 1,2,3,4-tetrahydro-N,N,9-trimethyl-1,4-ethanocarbazole-2-carboxamide (0.40 g, 0.0015 mole, described in Example 4) in anhydrous tetrahydrofuran (10 ml) was added dropwise to a stirred suspension of lithium aluminum hydride (0.050 g, 0.0015 mole) in anhydrous tetrahydrofuran (10 ml) under nitrogen at 0° C. Stirring was continued for 3 hr at room temperature and at reflux for one hr. The excess hydride was destroyed by dropwise addition of water to the cooled mixture (0° C.). Saturated sodium chloride solution was added and the compound was extracted with diethyl ether. The ether solution was extracted with dilute hydrochloric acid and the aqueous extract was basified with 10% aqueous sodium hydroxide. The alkaline solution was extracted with diethyl ether. The organic solution was dried and evaporated to dryness to afford a colorless oil of the title compound. Addition of a solution of hydrogen chloride in diethyl ether to a solution of the compound in diethyl ether gave the hydrochloride salt (0.35 g) of the title compound: mp 239°–241° C.; NMR (CDCl$_3$) δ 0.8–2.3 (m, 7H), 2.4–2.75 (m, 8H), 3.5–4.0 (m, 2H), 3.90 (s, 3H) and 6.9–7.7 (m, 4H); and Anal. Calcd for $C_{18}H_{24}N_2$·HCl: C, 70.91% H, 8.27% N, 9.19% and Found: C, 70.38% H, 8.28% N, 9.26%.

In the same manner, but replacing 1,2,3,4-tetrahydro-N,N,9-trimethyl-1,4-ethanocarbazole-2-carboxamide with another amide of formula V described in Example 4, the following compounds of formula I were obtained: 2-[(dimethylamino)methyl]-1,2,3,4-tetrahydro-1,4-ethanocarbazole 2-naphthalenesulfonate salt (I: $R^1$=H, $R^2$ and $R^3$=methyl and m=1): mp 237°–238° C. (crystallized from acetone); NMR (DMSO-d$_6$) δ 2.75 (s, 6H), 3.4 (m, 4H), 6.9–8.3 (m, 11H) and 11.0 (s, 1H); and Anal. Calcd for $C_{27}H_{30}N_2O_3S$: C, 70.11% H, 6.54% N, 6.06% and Found: C, 69.74% H, 6.58% N, 5.83%; 2-[(dimethylamino)methyl]-9-ethyl-1,2,3,4-tetrahydro-1,4-ethanocarbazole hydrochloride (I: $R^1$=ethyl, $R^2$ and $R^3$=methyl and m=1): mp 217°–218° C. (crystallized from acetone-diethyl ether); NMR (CDCl$_3$) δ 1.35 (t, 3H), 2.75 (d, 6H), 3.52–3.95 (br, 2H), 4.42 (m, 2H), 7.3 (m, 4H) and 11.8 (br, 1H); and Anal. Calcd for $C_{19}H_{26}N_2$·HCl: C, 71.56% H, 8.53% N, 8.79% and Found: C, 71.34% H, 8.71% N, 8.58%; and 1,2,3,4-tetrahydro-2-[(dimethylamino)methyl]-9-propyl-1,4-ethanocarbazole hydrochloride (I: $R^1$=propyl, $R^2$ and $R^3$=methyl and m=1): mp 247° C.; NMR (CDCl$_3$) δ 0.93 (t, 3H), 2.7–2.8 (d, 6H), 3.58 (br, 1H), 3.95 (br, 1H), 4.35 (m, 2H) and 7.3 (m, 4H); and Anal. Calcd for $C_{20}H_{28}N_2$·HCl: C, 72.13% H, 8.78% N, 8.41% and Found: C, 72.19% H, 8.82% N, 8.23%.

EXAMPLE 6

N-(9-Ethyl-2,3,4,9-tetrahydro-1,4-ethano-1H-carbazol-2-yl)-formamide (VI: $R^2$=H and $R^4$=ethyl)

To a stirred solution of 9-ethyl-1,2,3,4-tetrahydro-1,4-ethanocarbazole-2-carboxylic acid (5.0 g, 0.0186 mole, described in Example 3) in dry tetrahydrofuran (50 ml), under nitrogen at 20°–22° C., triethylamine (11.5 ml) was added, followed by ethyl chloroformate (2.8 ml) at 20° C. After stirring at room temperature for 3 hr, the suspension of mixed anhydride was cooled to −10° C. and treated dropwise with a solution of sodium azide (2.94 g in 10 ml of water). The slurries were stirred for 1 hr at −10° C. Water was added and saturated with sodium chloride, then extracted with diethyl ether. The organic layer was washed with water, dried, evaporated to give a yellow oil (ca. 5 g) of 9-ethyl-2,3,4,9-tetrahydro-1,4-ethano-1H-carbazole-2-carbonyl azide: IR (CHCl$_3$) 2135 cm$^{-1}$.

In the same manner, but replacing 9-ethyl-1,2,3,4-tetrahydro-1,4-ethanocarbazole-2-carboxylic acid with another carboxylic acid described in Examples 2 and 3, the following azides are obtained: 2,3,4,9-tetrahydro-1,4-ethano-1H-carbazole-2-carbonyl azide, 2,3,4,9-tetrahydro-9-methyl-1,4-ethano-1H-carbazole-2-carbonyl azide: IR (CHCl$_3$) 2135 cm$^{-1}$; and 2,3,4,9-tetrahydro-9-propyl-1,4-ethano-1H-carbazole-2-carbonyl azide.

A solution of 9-ethyl-2,3,4,9-tetrahydro-1,4-ethano-1H-carbazole-2-carbonyl azide (5 g, described above) in dry benzene (50 ml) was heated under nitrogen on a steam-bath for 3 hr and evaporated to give a residue of isocyanic acid, 9-ethyl-2,3,4,9-tetrahydro-1,4-ethano-1H-carbazol-2-yl ester: IR (CHCl$_3$) 2240 cm$^{-1}$.

In the same manner, but replacing 9-ethyl-2,3,4,9-tetrahydro-1,4-ethano-1H-carbazole-2-azide with another azide described above, the following isocyanates are obtained, respectively: isocyanic acid, 2,3,4,9-tetrahydro-1,4-ethano-1H-carbazol-2-yl ester; isocyanic acid, 2,3,4,9-tetrahydro-9-methyl-1,4-ethano-1H-carbazol-2-yl ester: IR (CHCl$_3$) 2240 cm$^{-1}$; and isocyanic acid, 2,3,4,9-tetrahydro-9-propyl-1,4-ethano-1H-carbazol-2-yl ester.

To a stirred suspension of sodium borohydride (2.0 g, 0.044 mole) in 20 ml of dimethoxyethane under nitrogen, a solution of isocyanic acid, 9-ethyl-2,3,4,9-tetrahydro-1,4-ethano-1H-carbazol-2-yl ester (4.2 g, 0.0158 mole, described above) in 30 ml of dimethoxyethane was added dropwise. The suspension was stirred for 20 hr at room temperature and concentrated under reduced pressure. The residue was treated with 1 N hydrochloric acid (caution: exothermic!) and extracted with ethyl acetate. The extract was washed with water, dried, evaporated to dryness to give a yellow foam (3.2 g). The foam was chromatographed on silica gel using a 5% acetone-benzene mixture to yield the title compound as a crystalline pale yellow compound (0.9 g): IR (CHCl$_3$) 3420 cm$^{-1}$.

In the same manner, but replacing isocyanic acid, 9-ethyl-2,3,4,9-tetrahydro-1,4-ethano-1H-carbazol-2-yl ester with another isocyanate described above, the following formamides of formula VI are obtained, respectively: N-(2,3,4,9-tetrahydro-1,4-ethano-1H-carbazol-2-yl)-formamide; N-(2,3,4,9-tetrahydro-9-methyl-1,4-ethano-1H-carbazol-2-yl)-formamide: NMR (CDCl$_3$) δ 0.7–2.5 (m, 6H), 3.65 (s, 3H), 4.0 (m, 1H), 7.0–7.6 (m, 4H) and 7.8 (s, 1H); and N-(2,3,4,9-tetrahydro-9-propyl-1,4-ethano-1H-carbazol-2-yl)-formamide.

EXAMPLE 7

N-(9-Ethyl-2,3,4,9-tetrahydro-1,4-ethano-1H-carbazol-2-yl)-N-methyl-formamide (VI: $R^2$=methyl and $R^4$=ethyl)

To a stirred suspension of sodium hydride (0.5 g of 57% oil dispersion, 0.011 mole) in dry xylene (15 ml), a solution of N-(9-ethyl-2,3,4,9-tetrahydro-1,4-ethano-1H-carbazol-2-yl)-formamide (0.9 g, 0.0034 mole, described in Example 6) in dry xylene (15 ml) was added dropwise under nitrogen. The suspension was refluxed with stirring for 18 hr. The reaction mixture was cooled. The water condenser was replaced by a dry ice/acetone condenser and methyl iodide (1.7 ml) was added. The reaction mixture was refluxed for 5 hr. Additional 1.7 ml of methyl iodide was added. The solution was refluxed for 4 hr and stirred at 20° C. for 18 hr. The reaction mixture was cooled in ice, and water was added dropwise to destroy the excess hydride. The compound was extracted with ethyl acetate and the organic layer was washed with water, dried and evaporated to afford the title compound as a yellow oil (ca. 1.2 g): IR (CHCl$_3$) 1650 cm$^{-1}$.

In the same manner, but replacing N-(9-ethyl-2,3,4,9-tetrahydro-1,4-ethano-1H-carbazol-2-yl)-formamide with another formamide of formula VI described in Example 6, the following N-methyl-formamides of formula VI were obtained, respectively: N-(2,3,4,9-tetrahydro-1,4-ethano-1H-carbazol-2-yl)-N-methyl-formamide; N-(2,3,4,9-tetrahydro-9-methyl-1,4-ethano-1H-carbazol-2-yl)-N-methyl-formamide: NMR (CDCl$_3$) δ 2.00–2.06 (m, 3H), 3.70 (s, 3H), 7.30 (m, 4H) and 8.02–8.07 (m, 1H); and N-(2,3,4,9-tetrahydro-9-propyl-1,4-ethano-1H-carbazol-2-yl)-N-methyl-formamide.

EXAMPLE 8

9-Ethyl-1,2,3,4-tetrahydro-N,N-dimethyl-1,4-ethanocarbazole-2-amine (I: $R^1$=ethyl, $R^2$ and $R^3$=methyl and m=0)

To a suspension of lithium aluminum hydride (0.6 g) in dry tetrahydrofuran (15 ml), a solution of N-(9-ethyl-2,3,4,9-tetrahydro-1,4-ethano-1H-carbazol-2-yl)-N-methyl-formamide (1.0 g, 0.0036 mole, described in Example 7) in dry tetrahydrofuran (20 ml) was added dropwise with ice-cooling under nitrogen. The suspension was stirred at room temperature for 3 hr and cooled in ice bath. The excess hydride was destroyed by adding dropwise ethyl acetate, then a saturated potassium sodium tartrate solution. The solution was decanted and the residue was washed with ethyl acetate. The solvents were evaporated and the residue was taken up in diethyl ether. The solution was extracted with dilute hydrochloric acid and the aqueous extract was rendered basic with dilute sodium hydroxide. After extraction with diethyl ether, the ether extract was dried and evaporated to give the title compound (0.9 g). A solution of hydrogen chloride in diethyl ether was added to a solution of the title compound in diethyl ether. The precipitate was collected and crystallized from a mixture of methanol-chloroform-diethyl ether to give the hydrochloride salt (0.7 g) of the title compound: mp 215°–216° C.: NMR (CDCl$_3$) δ 1.40 (t, 3H), 1.94 (d, 3H), 2.56 (d, 3H), 4.43 (q, 2H) and 7.0–7.8 (m, 4H); and Anal. Calcd for C$_{18}$H$_{24}$N$_2$.HCl: C, 70.91% H, 8.27% N, 9.19% and Found: C, 70.66% H, 8.16% N, 8.93%.

In the same manner, but replacing N-(9-ethyl-2,3,4,9-tetrahydro-1,4-ethano-1H-carbazol-2-yl)-N-methyl-formamide with another N-methylformamide of formula VI described in Example 7, the following compounds of formula I are obtained, respectively: 1,2,3,4-tetrahydro-N,N-dimethyl-1,4-ethanocarbazole-2-amine (I: $R^1$ is hydrogen, $R^2$ and $R^3$=methyl and m=0); 1,2,3,4-tetrahydro-N,N,9-trimethyl-1,4-ethanocarbazole-2-amine hydrochloride (I: $R^1$, $R^2$ and $R^3$=methyl and m=0): mp 210°–211° C.; NMR (CDCl$_3$) δ 1.98 (d, 3H), 2.60 (d, 3H), 3.88 (s, 3H) and 7.0–7.20 (m, 4H); and Anal. Calcd for C$_{17}$H$_{22}$N$_2$.HCl: C, 70.19% H, 7.97% N, 9.63% and Found: C, 69.72% H, 7.98% N, 9.39% and 1,2,3,4-tetrahydro-N,N-dimethyl-9-propyl-1,4-ethanocarbazole-2-amine.

EXAMPLE 9

1,2,3,4-Tetrahydro-N,9-dimethyl-1,4-ethanocarbazole-2-amine (I: $R^1$ and $R^2$=methyl, $R^3$=H and m=0)

A solution of N-(2,3,4,9-tetrahydro-1,4-ethano-1H-carbazol-2-yl)-N-methyl-formamide (3.9 g, 0.0145 mole, described in Example 7) in 20 ml of 10% sodium hydroxide and 40 ml ethanol was refluxed under nitrogen on a steam-bath for 5 hr. The solution was evaporated to dryness and the residue was taken up in diethyl ether. The organic layer was washed (3×) with 2 N hydrochloric acid and the acidic layer was washed with diethyl ether. The aqueous layer was made basic with 25% sodium hydroxide and extracted with diethyl ether. The ether extract was washed with water, dried, evaporated to afford the title compound as a pale yellow oil (3 g): NMR (CDCl$_3$) δ 1.0 (s, 1H), 2.32 (3, 3H), 3.75 (s, 3H) and 2.1–7.7 (m, 4H). It was chromatographed on silica gel and eluted with 5% methanol-chloroform to give a pale yellow oil (2.2 g) which was dissolved in dichloromethane and treated with a solution of hydrogen chloride in diethyl ether to form a gummy precipitate. The residue was crystallized from methanol-dichloromethane-diethyl ether to yield a greenishgray compound (2.0 g). Recrystallization from methanol-dichloromethanediethyl ether afforded the hydrochloride salt of the title compound as an off-white powder (1.95 g): mp 204°–205° C.; and Anal. Calcd for C$_{16}$H$_{20}$N$_2$.HCl: C, 69.41% H, 7.65% N, 10.12% and Found: C, 69.25% H, 7.55% N, 9.89%.

EXAMPLE 10

1,2,3,4-Tetrahydro-9-methyl-1,4-ethanocarbazole-2-amine (I: $R^1$=methyl, $R^2$ and $R^3$=H and m=0)

A solution of N-(2,3,4,9-tetrahydro-1,4-ethano-1H-carbazol-2-yl)-formamide (2.5 g, 0.01 mole, described in Example 6) in 10 ml 10% sodium hydroxide and 20 ml ethanol was refluxed under nitrogen on a steam-bath for 15 hr and evaporated to give a residue of the title compound. A solution of the residue in diethyl ether was extracted with dilute hydrochloric acid and the aqueous extract was rendered basic with dilute sodium hydroxide. The aqueous solution was extracted with diethyl ether. The ether extract was dried and mixed with a solution of hydrogen chloride in diethyl ether. The precipitate was collected and crystallized from chloroform-methanol-diethyl ether to give the hydrochloride salt of the title compound (1.4 g): mp 180° C. dec.; NMR (CDCl$_3$) δ 3.8 (s, 3H), 7.0–7.7 (m, 4H) and 8.05 (br, 3H); and Anal. Calcd for C$_{15}$H$_{18}$N$_2$.HCl: C, 68.55% H, 7.29% N, 10.66% and Found: C, 67.47% H, 7.30% N, 10.36%.

We claim:

1. A compound of the formula

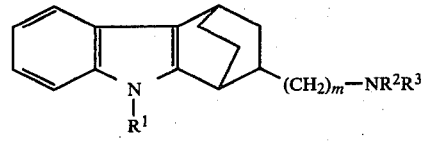

in which $R^1$ is hydrogen or lower alkyl, $R^2$ and $R^3$ each is hydrogen or lower alkyl or $R^2$ and $R^3$ together with the nitrogen atom form a 1-pyrrolidinyl, 1-piperidinyl, 1-piperazinyl, 4-morpholinyl or 4-thiomorpholinyl ring, and m is an integer from 0 to 3; or a therapeutically acceptable acid addition salt thereof.

2. A compound of claim 1 in which $R^1$, $R^2$ and $R^3$ each is hydrogen or lower alkyl, and m is the integer 0 or 1; or a therapeutically acceptable acid addition salt thereof.

3. A compound of claim 1 in which $R^1$ is hydrogen or lower alkyl, $R^2$ and $R^3$ each is lower alkyl, and m is the integer 1; or a therapeutically acceptable acid addition salt thereof.

4. 2-[(Dimethylamino)methyl]-1,2,3,4-tetrahydro-9-methyl-1,4-ethanocarbazole, a compound of claim 1 wherein $R^1$, $R^2$ and $R^3$ are methyl and m=1.

5. 2-[(Dimethylamino)methyl]-1,2,3,4-tetrahydro-1,4-ethanocarbazole, a compound of claim 1 wherein $R^1$ is hydrogen, $R^2$ and $R^3$ are methyl and m=1.

6. 2-[(Dimethylamino)methyl]-9-ethyl-1,2,3,4-tetrahydro-1,4-ethanocarbazole, a compound of claim 1 wherein $R^1$ is ethyl, $R^2$ and $R^3$ are methyl and m=1.

7. 2-[(Dimethylamino)methyl]-1,2,3,4-tetrahydro-9-propyl-1,4-ethanocarbazole, a compound of claim 1 wherein $R^1$ is propyl, $R^2$ and $R^3$ are methyl and m=1.

8. 9-Ethyl-1,2,3,4-tetrahydro-N,N-dimethyl-1,4-ethanocarbazole-2-amine, a compound of claim 1 wherein $R^1$ is ethyl, $R^2$ and $R^3$ are methyl and m=0.

9. 1,2,3,4-Tetrahydro-N,N,9-trimethyl-1,4-ethanocarbazole-2-amine, a compound of claim 1 wherein $R^1$, $R^2$ and $R^3$ are methyl and m=0.

10. 1,2,3,4-Tetrahydro-N,9-dimethyl-1,4-ethanocarbazole-2-amine, a compound of claim 1 wherein $R^1$ and $R^2$ are methyl, $R^3$ is hydrogen and m=0.

11. 1,2,3,4-Tetrahydro-9-methyl-1,4-ethanocarbazole-2-amine, a compound of claim 1 wherein $R^1$ is methyl, $R^2$ and $R^3$ are hydrogen and m=0.

12. A method of treating depression in a mammal, which comprises administering to a mammal in need thereof, an effective antidepressant amount of a compound of claim 1 or a therapeutically acceptable acid addition salt thereof.

13. A pharmaceutical composition comprising an antidepressant effective amount of a compound of claim 1, or a therapeutically acceptable acid addition salt thereof, and a pharmaceutically acceptable carrier.

* * * * *